(12) United States Patent
Daniels

(10) Patent No.: US 10,883,046 B2
(45) Date of Patent: Jan. 5, 2021

(54) SYNTHESIS OF LUMINESCENT 2D LAYERED MATERIALS USING AN AMINE-MET AL COMPLEX AND A SLOW SULFUR-RELEASING PRECURSOR

(71) Applicant: Nanoco Technologies Ltd., Manchester (GB)

(72) Inventor: Steven Daniels, Manchester (GB)

(73) Assignee: Nanoco 2D Materials Limited, Manchester (GB)

(*) Notice: Subject to any disclaimer, the term of this patent is extended or adjusted under 35 U.S.C. 154(b) by 439 days.

(21) Appl. No.: 15/879,136

(22) Filed: Jan. 24, 2018

(65) Prior Publication Data

US 2018/0216000 A1  Aug. 2, 2018

Related U.S. Application Data

(60) Provisional application No. 62/453,780, filed on Feb. 2, 2017, provisional application No. 62/588,774, filed on Nov. 20, 2017.

(51) Int. Cl.

| | |
|---|---|
| C09K 11/68 | (2006.01) |
| C09K 11/02 | (2006.01) |
| C07C 211/08 | (2006.01) |
| B82Y 20/00 | (2011.01) |
| C07F 11/00 | (2006.01) |
| C01B 19/00 | (2006.01) |
| C07C 211/03 | (2006.01) |
| C01B 17/20 | (2006.01) |
| C07C 211/21 | (2006.01) |
| C01G 39/06 | (2006.01) |
| B82Y 30/00 | (2011.01) |
| B82Y 40/00 | (2011.01) |

(52) U.S. Cl.
CPC ............ *C09K 11/681* (2013.01); *B82Y 20/00* (2013.01); *C01B 17/20* (2013.01); *C01B 19/007* (2013.01); *C01G 39/06* (2013.01); *C07C 211/03* (2013.01); *C07C 211/08* (2013.01); *C07C 211/21* (2013.01); *C07F 11/005* (2013.01); *C09K 11/02* (2013.01); *B82Y 30/00* (2013.01); *B82Y 40/00* (2013.01); *C01P 2004/24* (2013.01); *C01P 2004/64* (2013.01)

(58) Field of Classification Search
CPC ....... C09K 11/681; B82Y 20/00; B82Y 30/00; B82Y 40/00; C01B 17/20; C01B 19/007; C01G 39/06
See application file for complete search history.

(56) References Cited

U.S. PATENT DOCUMENTS

| | | |
|---|---|---|
| 7,309,680 B2 | 12/2007 | John et al. |
| 9,193,604 B2 | 11/2015 | Kamiya et al. |
| 9,359,202 B2 | 6/2016 | Gresty et al. |
| 10,221,356 B2 | 3/2019 | Ghosh et al. |
| 2009/0159849 A1 | 6/2009 | Uehara et al. |
| 2010/0034728 A1 | 2/2010 | Seo et al. |
| 2010/0213420 A1 | 8/2010 | Kamiya et al. |
| 2014/0011317 A1 | 1/2014 | Gresty et al. |
| 2017/0029697 A1 | 2/2017 | Ghosh et al. |

FOREIGN PATENT DOCUMENTS

| | | |
|---|---|---|
| CA | 2432993 A1 | 8/2004 |
| CN | 105129748 A | 12/2012 |
| CN | 103896222 A | 7/2014 |
| CN | 106395765 A | 2/2017 |
| JP | 2009161372 A | 7/2009 |
| WO | 2018002607 A2 | 4/2018 |
| WO | 2018122667 A1 | 7/2018 |

OTHER PUBLICATIONS

Joo et al, "Gernaeralzed and Facile Sythesis or Semiconductor Metal Sulfide Nanocrystals", J. Am. Chem. Soc., 125, 2003, pp. 11100-11105, Aug. 13, 2003.*

PCT Int'l Search Report received in copending PCT Application No. PCT/IB2018/050465 dated May 9, 2018, 11 pages.

Jin Joo et al: "Generalized and Facile Synthesis of Semiconducting Metal Sulfide Nanocrystals", Journal of The American Chemical Society, vol. 125, No. 36, Sep. 1, 2003 (Sep. 1, 2003 ), pp. 11100-11105, XP055408080, ISSN: 0002-7863, DOI: 10.1021 /ja0357902.

Ludovico Cademartiri et al: "Large-Scale Synthesis of Ultrathin Bi2S3 Necklace Nanowires", Angewandte Chemie International Edition, vol. 47, No. 20, May 5, 2008 (May 5, 2008), pp. 3814-3817, XP055468240, ISSN: 1433-7851, DOI: 10.1002/anie. 200705034 & Supporting Information, XP055468242, Retrieved from the Internet: URL:https://application.wiley-vch.de/contents/jc_2002/2008/z705034_s.pdf.

Haesuk Hwang et al: "MoS2 Nanoplates Consisting of Disordered Graphene-like Layers for High Rate Lithium Battery Anode Materials", Nano Letters, vol. 11, No. 11, Nov. 9, 2011 (Nov. 9, 2011), pp. 4826-4830, XP055468120, ISSN: 1530-6984, DOI: 10.1021 /nl202675f.

(Continued)

*Primary Examiner* — C Melissa Koslow

(74) *Attorney, Agent, or Firm* — Blank Rome LLP

(57) ABSTRACT

A method of synthesis of two-dimensional (2D) nanoparticles comprises combining a first nanoparticle precursor and a second nanoparticle precursor in one or more solvents to form a solution, followed by heating the solution to a first temperature for a first time period, then subsequently heating the solution to a second temperature for a second time period, wherein the second temperature is higher than the first temperature, to effect the conversion of the nanoparticle precursors into 2D nanoparticles. In one embodiment, the first nanoparticle precursor is a metal-amine complex and the second nanoparticle precursor is a slow-releasing chalcogen source.

5 Claims, 2 Drawing Sheets

(56) References Cited

OTHER PUBLICATIONS

Li H et al: "Electrochemical lithiation/delithiation performances of 3D flowerlike MoS2 powders prepared by ionic iquid assisted hydrothermal route", Journal of Alloys and Compounds, Elsevier Sequoia, Lausanne, CH, vol. 471, No. 1-2, Mar. 5, 2009 (Mar. 5, 2009), pp. 442-447, XP025994443, ISSN: 0925-8388, DOI: 10.1016/J.JALLCOM. 2008.03.133.

Dennenberg, R. J. et al.; "Infrared and Kinetic Studies of Group VI Metal Pentacarbonyl Amine Compounds"; Inorganic Chemistry; vol. 11; No. 1; 1972; pp. 72-77.

Kraihanzel, C.S. et al.; "Vibrational Spectra and Bonding in Metal Carbonyls. II. Infrared Spectra of Amine-Substituted Group VI Carbonyls in the CO Stretching Region"; Infrared Spectra of Amine-Substituted Carbonyls; vol. 2; No. 3; Jun. 1963; pp. 533-540.

Lin, Huihui et al.; "Colloidal Synthesis of MoS2 Quantum Dots: Size-dependent Tunable Photoluminescence and Bioimaging"; The Royal Society of Chemistry; 2013; vol. 00; pp. 1-6.

Taiwanese Search Report received in copending Taiwanese Application No. 107103901 dated Oct. 5, 2018, 2 pages with translation.

Aliaga, Juan Antonio, et al. "Rhenium and molybdenum poorly crystalline disulfides and their mesophases with hexadecylamine," Journal of Coordination Chemistry 67.23-24 (2014): 3884-3893.

Ghosh, Sirshendu et al.; "Fabrication of tungsten nanocrystals and silver-tungsten nanonets: a potent reductive catalyst"; RSC Advances; vol. 5; 2015; pp. 38971-38976.

Kuzuya, Toshihiro et al.; "Synthesis of Zinc Sulfide Nanocrystals and Fabrication of Nanocrystal Superlattice"; Materials Transactions; vol. 45; No. 8; 2004; pp. 2650-2652.

Lin, Huihui et al.; "Colloidal Synthesis of MoS2 Quantum Dots: Size-dependent Tunable Photoluminescence and Bioimaging"; New J. Chem., 2015, 39, 8492-8497.

Novoselov, K.S. et al.; "Electric Field Effect in Atomically Thin Carbon Films"; Science; Oct. 22, 2004; vol. 306; pp. 666-669.

\* cited by examiner

SYNTHESIS OF LUMINESCENT 2D LAYERED MATERIALS USING AN AMINE-METAL COMPLEX AND A SLOW SULFUR-RELEASING PRECURSOR

CROSS-REFERENCE TO RELATED APPLICATIONS

This application claims the benefit of U.S. Provisional Application Ser. No. 62/453,780, filed Feb. 2, 2017, and U.S. Provisional Application Ser. No. 62/588,774, filed Nov. 20, 2017, the contents of which are hereby incorporated by reference in their entireties.

STATEMENT REGARDING FEDERALLY SPONSORED RESEARCH OR DEVELOPMENT

Not Applicable

BACKGROUND OF THE INVENTION

1. Field of the Invention

The present invention generally relates to two-dimensional (2D) materials. More particularly, it relates to 2D nanoparticles.

2. Description of the Related Art Including Information Disclosed Under 37 CFR 1.97 and 1.98

The isolation of graphene via the mechanical exfoliation of graphite [K. S. Novoselov, A. K. Geim, S. V. Morozov, D. Jiang, Y. Zhang, S. V. Dubnos, I. V. Grigorieva and A. A. Firsov, *Science,* 2004, 306, 666] has sparked strong interest in two-dimensional (2D) layered materials. The properties of graphene include exceptional strength, and high electrical and thermal conductivity, while being lightweight, flexible and transparent. This opens the possibility of a wide array of potential applications, including high speed transistors and sensors, barrier materials, solar cells, batteries, and composites.

Other classes of 2D materials of widespread interest include transition metal dichalcogenide (TMDC) materials, hexagonal boron nitride (h-BN), as well as those based on Group 14 elements, such as silicene and germanene. The properties of these materials can range from semi-metallic, for example, $NiTe_2$ and $VSe_2$, to semiconducting, for example, $WSe_2$ and $MoS_2$, to insulating, for example, h-BN. 2D nanosheets of TMDC materials are of increasing interest for applications ranging from catalysis to sensing, energy storage and optoelectronic devices.

TMDC monolayers are atomically thin semiconductors of the type MX2, where M a transition metal element (Mo, W, etc.) and X a chalcogen element (S, Se, or Te). A single layer of M atoms is sandwiched between two layers of X atoms. A $MoS_2$ monolayer is 6.5 Å thick. Of the 2D TMDCs, the semiconductors $WSe_2$ and $MoS_2$ are of particular interest because, while largely preserving their bulk properties, additional properties arise due to quantum confinement effects when the dimensions of the materials are reduced to mono- or few layers. In the case of $WSe_2$ and $MoS_2$, these include the exhibition of an indirect-to-direct band gap transition, with strong excitonic effects, when the thickness is reduced to a single monolayer. This leads to a strong enhancement in photoluminescence efficiency, opening new opportunities for the application of such materials in optoelectronic devices. Other materials of particular interest include $WS_2$ and $MoSe_2$.

The discovery of graphene illustrates how new physical properties may emerge when a bulk crystal of macroscopic dimensions is thinned down to one atomic layer. Like graphite, TMDC bulk crystals are formed of monolayers bound to each other by van der Waals attraction. TMDC monolayers have properties that are distinctly different from those of the semi-metal graphene. For example, TMDC monolayers $MoS_2$, $WS_2$, $MoSe_2$, $WSe_2$ and $MoTe_2$ have a direct band gap, and can be used in electronics as transistors and in optics as emitters and detectors. Group 4 to 7 TMDCs predominantly crystallise in layered structures, leading to anisotropy in their electrical, chemical, mechanical and thermal properties. Each layer comprises a hexagonally packed layer of metal atoms sandwiched between two layers of chalcogen atoms via covalent bonds. Neighboring layers are weakly bound by van der Waals interactions, which may easily be broken by mechanical or chemical methods to create mono- and few-layer structures.

The TMDC monolayer crystal structure has no inversion center, which allows access to a new degree of freedom of charge carriers, namely the k-valley index, and to open up a new field of physics: "valleytronics."

The strong spin-orbit coupling in TMDC monolayers leads to a spin-orbit splitting of hundreds meV in the valence band and a few meV in the conduction band, which allows control of the electron spin by tuning the excitation laser photon energy.

The work on TMDC monolayers is an emerging research and development field since the discovery of the direct bandgap and the potential applications in electronics and valley physics. TMDCs may be combined with other 2D materials like graphene and hexagonal boron nitride to make van der Waals heterostructure devices.

A semiconductor can absorb photons with energy larger than or equal to its bandgap. This means that light with a shorter wavelength is absorbed. Semiconductors are typically efficient emitters if the minimum of the conduction band energy is at the same position in k-space as the maximum of the valence band, i.e., the band gap is direct. The band gap of bulk TMDC material down to a thickness of two monolayers is still indirect, so the emission efficiency is lower compared to monolayered materials. The emission efficiency is about $10^4$ times greater for a TMDC monolayer than for bulk material. The band gaps of TMDC monolayers are in the visible range (between 400 nm and 700 nm). The direct emission shows two transitions called A and B, separated by the spin-orbit coupling energy. The lowest energy and therefore most important in intensity is the A emission. Owing to their direct band gap, TMDC monolayers are promising materials for optoelectronics applications.

In its multilayer form, $MoS_2$ is a silvery black solid that occurs as the mineral molybdenite—the principal ore for molybdenum. $MoS_2$ is relatively unreactive. It is unaffected by dilute acids and oxygen. $MoS_2$ is similar to graphite in its appearance and feel. It is widely used as a solid lubricant due to its low-friction properties and robustness. As a TMDC, $MoS_2$ possesses some of graphene's desirable qualities (such as mechanical strength and electrical conductivity), and can emit light, opening possible applications such as photodetectors and transistors.

For high-performance applications, flat, defect-free material is required, whereas for applications in batteries and supercapacitors, defects, voids and cavities are desirable.

Mono- and few-layer 2D nanosheets may be produced using "top-down" and "bottom-up" approaches. Top-down approaches involve the removal of layers, either mechanically or chemically, from the bulk material. Such techniques include mechanical exfoliation, ultrasound-assisted liquid phase exfoliation (LPE), and intercalation techniques. Bottom-up approaches, wherein 2D layers are grown from their constituent elements, include chemical vapor deposition (CVD), atomic layer deposition (ALD), and molecular beam epitaxy (MBE), as well as solution-based approaches including hot-injection.

A number of approaches to synthesize 2D nanosheets have been described in the prior art, the most common of which include mechanical exfoliation, LPE and CVD, with a small number of reports of solution-based approaches predominantly utilizing hot-injection techniques. While mechanical exfoliation provides highly crystalline flakes, the process is low yielding, offers poor thickness control and is unscalable. LPE offers a scalable route to the production of 2D nanosheets, and may be carried out under ambient conditions using less hazardous chemicals than other techniques. However, as with mechanical exfoliation, it provides poor thickness control, along with low reaction yields, and produces small flakes. Poor reaction yields are also typical of CVD syntheses. Advantages of this method include large area scalability, uniformity and thickness control. However, the quality of the resulting material is not comparable to that of mechanically exfoliated flakes, with the so-produced flakes typically being small and displaying poor long-term stability. Solution-based synthetic approaches are of increasing interest and have the potential to provide control over the size, shape and uniformity of the resulting 2D materials. Yet, further improvements are required to provide the ultimate combination of a scalable method of synthesis that generates flakes with the desired crystallographic phase, tunable and narrow size and shape distributions, and capped with a volatile ligand.

There are few literature reports of the colloidal synthesis of 2D quantum dots made via a "bottom up" approach. Most are "top down" exfoliation-based methods—i.e. methods wherein a bulk material is exfoliated to provide a 2D material. Solution-based approaches for the formation of 2D flakes are highly desirable, as they may offer control over the size, shape and uniformity of the resulting materials, as well as enabling ligands to be applied to the surface of the materials to provide solubility and, thus, solution processability. The application of organic ligands to the surface of the materials may also limit the degradation, as observed for CVD-grown samples, by acting as a barrier to oxygen and other foreign species. The resulting materials are free-standing, further facilitating their processability. However, the solution-based methods thus far developed do not provide a scalable reaction to generate 2D layered materials with the desired crystallographic phase, tunable narrow shape and size distributions and a volatile capping ligand, which is desirable in that it can be easily removed during device processing. One promising reference for $MoS_2$ used the single-source precursor ammonium tetrathiomolybdate $((NH_4)_2MoS_4)$. [H. Lin, C. Wang, J. Wu, Z. Xu, Y. Huang and C. Zhang, New J. Chem., 2015, 39, 8492] However, the reported method produces an insoluble material. It is contemplated that an organic-soluble material would be highly advantageous for certain applications and/or ease of use.

One of the challenges in the production of 2D layered materials is to achieve compositional uniformity, whether high-quality, defect-free, or defect-containing material is required, on a large scale. Further challenges include forming 2D flakes with a homogeneous shape and size distribution.

Thus, there is a need for a synthesis method that produces 2D nanoparticles with uniform properties that can be solution-processed.

BRIEF SUMMARY OF THE INVENTION

Herein, a method to prepare nanoparticles is described. The method may be used to produce 2D nanoparticles with uniform properties, which may be solution-processed.

In one embodiment, the method of synthesis comprises combining a first nanoparticle precursor and a second nanoparticle precursor in one or more solvents to form a solution, followed by heating the solution to a first temperature for a first time period, then subsequently heating the solution to a second temperature for a second time period, wherein the second temperature is higher than the first temperature, to effect the conversion of the nanoparticle precursors into 2D nanoparticles.

In one embodiment, the first nanoparticle precursor is a metal-amine complex. In one embodiment, the second nanoparticle precursor is a slow-releasing chalcogen source.

In one embodiment, the method of synthesis comprises dissolving a single-source precursor in a solvent to form a solution, heating the solution to a first temperature for a first time period, then subsequently heating the solution to a second temperature for a second time period, wherein the second temperature is higher than the first temperature, to effect the conversion of the single-source precursor into 2D nanoparticles.

In one embodiment, the 2D nanoparticles are TMDC nanoparticles.

In one embodiment, the 2D nanoparticles are 2D quantum dots (QD).

BRIEF DESCRIPTION OF THE SEVERAL VIEWS OF THE DRAWING(S)

DETAILED DESCRIPTION OF THE INVENTION

Figure 1:
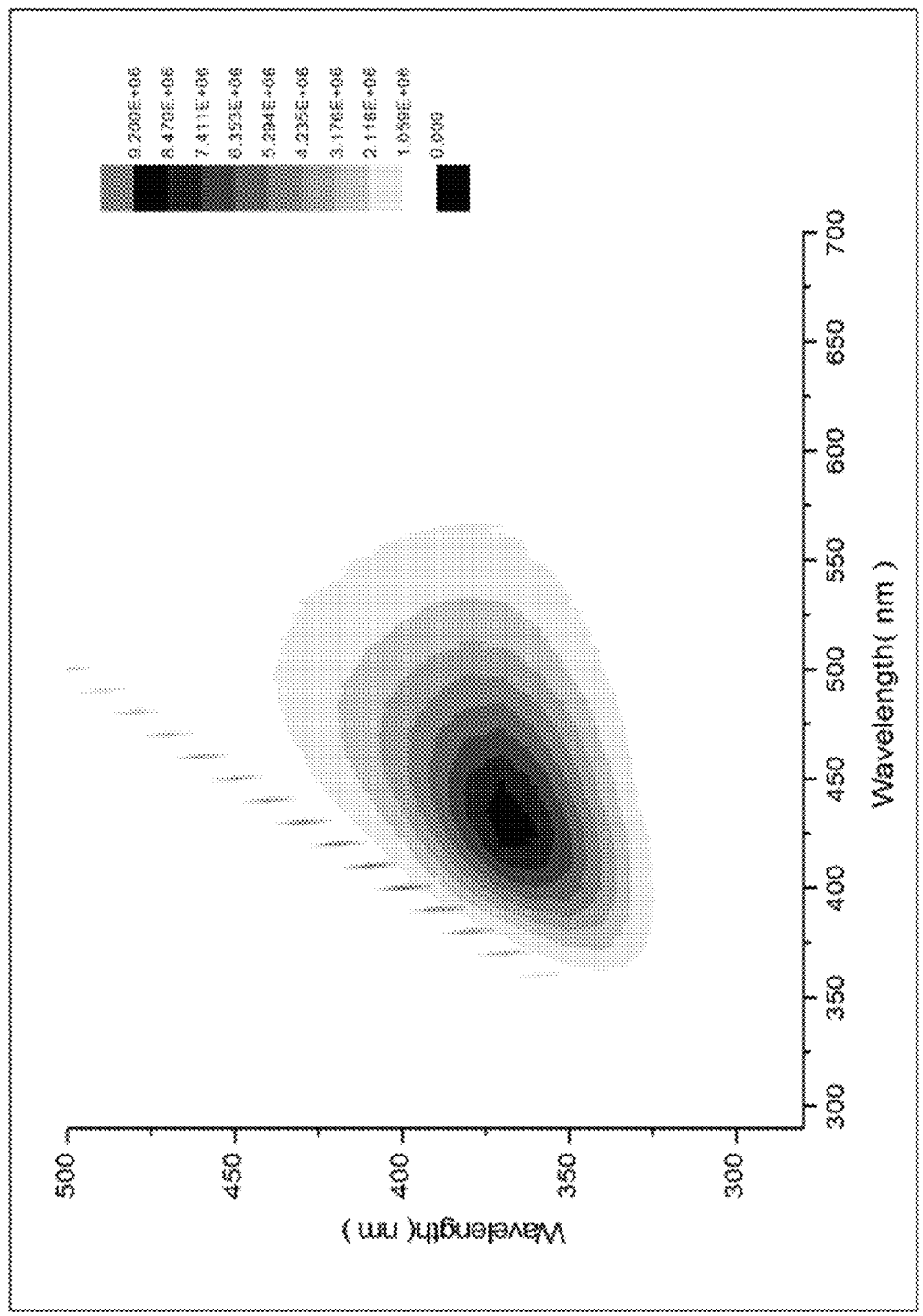
FIG. 1 is a photoluminescence contour map of $MoS_2$ 2D nanoparticles prepared according to Example 4.

Herein, a method to prepare nanoparticles is described. The process can be used to produce 2D nanoparticles with uniform properties. In one embodiment, the 2D nanoparticles are prepared via a one-pot method.

As used herein, the term "nanoparticle" is used to describe a particle with dimensions on the order of approximately 1 to 100 nm. The term "quantum dot" (QD) is used to describe a semiconductor nanoparticle displaying quantum confinement effects. The dimensions of QDs are typically, but not exclusively, between 1 to 10 nm. The terms "nanoparticle" and "quantum dot" are not intended to imply any restrictions on the shape of the particle. The term "2D nanoparticle" is used to describe a particle with lateral dimensions on the order of approximately 1 to 100 nm and a thickness between 1 to 10 atomic or molecular layers, and wherein the lateral dimensions are greater than the thickness. The term "2D nanoflake" is used to describe a particle with lateral dimensions on the order of approximately 1 to 100 nm and a thickness between 1 to 5 atomic or molecular layers.

As used herein, the term "one-pot method" is used to describe a method of synthesis wherein the nanoparticle precursors are converted to 2D nanoparticles in a single reaction vessel.

The composition of the nanoparticles is unrestricted. Suitable materials include, but are not restricted to:

graphene oxide and reduced graphene oxide;

transition metal dichalcogenides (TMDCs) such as, for example, $WO_2$; $WS_2$; $WSe_2$; $WTe_2$; $MnO_2$; $MoO_2$; $MoS_2$; $MoSe_2$; $MoTe_2$; $NiO_2$; $NiTe_2$; $NiSe_2$; $VO_2$; $VS_2$; $VSe_2$; $TaS_2$; $TaSe_2$; $RuO_2$; $RhTe_2$; $PdTe_2$; $HfS_2$; $NbS_2$; $NbSe_2$; $NbTe_2$; $FeS_2$; $TiO_2$; $TiS_2$; $TiSe_2$; and $ZrS_2$;

transition metal trichalcogenides such as, for example, $TaO_3$; $MnO_3$; $WO_3$; $ZrS_3$; $ZrSe_3$; $HfS_3$; and $HfSe_3$;

Group 13-16 (III-VI) compounds such as, for example, InS; InSe; GaS; GaSe; and GaTe;

Group 15-16 (V-VI) compounds such as, for example, $Bi_2Se_3$; and $Bi_2Te_3$;

nitrides such as, for example, h-BN;

oxides such as, for example, $LaVO_3$; $LaMnO_3$; $V_2O_5$; $LaNbO_7$; $Ca_2Nb_3O_{10}$; $Ni(OH)_2$; and $Eu(OH)_2$; layered copper oxides; micas; and bismuth strontium calcium copper oxide (BSCCO);

phosphides such as, for example, $Li_7MnP_4$; and $MnP_4$.

In the aforementioned materials, adjacent layers are held together by van der Waals interactions, which can readily be separated during synthesis to form 2D flakes. In alternative embodiments, the nanoparticles comprise non-layered semiconductor materials, including, but not restricted to:

Group 12-16 (II-VI) semiconductors such as, for example, ZnS; ZnSe; CdS; CdSe; CdTe;

Group 13-15 (III-V) materials such as, for example, GaN; GaP; GaAs; InN; InP; InAs; and Group I-II-VI materials such as, for example, $CuGaS_2$; $CuGaSe_2$; $CuGa(S,Se)_2$; $CuInS_2$; $CuInSe_2$; $CuIn(S,Se)_2$; $Cu(In,Ga)S_2$; $Cu(In,Ga)Se_2$; $Cu(In,Ga)(S,Se)_2$; $CuInTe_2$; $AgInS_2$; and $AgInSe_2$; and including doped species and alloys thereof.

In some embodiments, the 2D nanoparticles are 2D nanoflakes. In some embodiments, the 2D nanoparticles are 2D QDs. QDs have widely been investigated for their unique optical, electronic and chemical properties, which originate from "quantum confinement effects"—as the dimensions of a semiconductor nanoparticle are reduced below twice the Bohr radius, the energy levels become quantized, giving rise to discrete energy levels. The band gap increases with decreasing particle size, leading to size-tunable optical, electronic and chemical properties, such as size-dependent photoluminescence. Moreover, it has been found that reducing the lateral dimensions of a 2D nanoflake into the quantum confinement regime may give rise to yet further unique properties, depending on both the lateral dimensions and the number of layers of the 2D nanoflake. In some embodiments, the lateral dimensions of the 2D nanoflakes may be in the quantum confinement regime, wherein the optical, electronic and chemical properties of the nanoparticles may be manipulated by changing their lateral dimensions. For example, metal chalcogenide monolayer nanoflakes of materials such as $MoSe_2$ and $WSe_2$ with lateral dimensions of approximately 10 nm or less may display properties such as size-tunable emission when excited. This can enable the electroluminescence maximum ($EL_{max}$) or photo-luminescence ($PL_{max}$) of the 2D nanoflakes to be tuned by manipulating the lateral dimensions of the nanoparticles. As used herein, a "2D quantum dot" or "2D QD" refers to a semiconductor nanoparticle with lateral dimensions in the quantum confinement regime and a thickness between 1-5 atomic or molecular monolayers. As used herein, a "single-layered quantum dot" or "single-layered QD" refers to a semiconductor nanoparticle with lateral dimensions in the quantum confinement regime and a thickness of a single monolayer. Compared with conventional QDs, 2D QDs have a much higher surface area-to-volume ratio, which increases as the number of monolayers is decreased. The highest surface area-to-volume ratio is seen for single-layered QDs. This may lead to 2D QDs having very different surface chemistry from conventional QDs, which may be exploited for applications such as catalysis.

In one embodiment, the method of synthesis comprises combining a first nanoparticle precursor and a second nanoparticle precursor in one or more solvents to form a solution, followed by heating the solution to a first temperature for a first time period, then subsequently heating the solution to a second temperature for a second time period, wherein the second temperature is higher than the first temperature, to effect the conversion of the nanoparticle precursors into 2D nanoparticles.

In an alternative embodiment, the method of synthesis comprises dissolving a single-source precursor in a solvent to form a solution, heating the solution to a first temperature for a first time period, then subsequently heating the solution to a second temperature for a second time period, wherein the second temperature is higher than the first temperature, to effect the conversion of the single-source precursor into 2D nanoparticles.

In one embodiment, the first precursor is a metal precursor. Suitable metal precursors may include, but are not restricted to, inorganic precursors, for example:

metal halides such as $WCl_n$ (n=4-6), $Mo_6Cl_{12}$, $MoCl_3$, $[MoCl_5]_2$, $NiCl_2$, $MnCl_2$, $VCl_3$, $TaCl_5$, $RuCl_3$, $RhCl_3$, $PdCl_2$, $HfCl_4$, $NbCl_5$, $FeCl_2$, $FeCl_3$, $TiCl_4$, $SrCl_2$, $SrCl_2.6H_2O$, $WO_2Cl_2$, $MoO_2Cl_2$, $Cu Cl_2$, $ZnCl_2$, $CdCl_2$, $GaCl_3$, $InCl_3$, $WF_6$, $MoF_6$, $NiF_2$, $MnF_2$, $TaF_5$, $NbF_5$, $FeF_2$, $FeF_3$, $TiF_3$, $TiF_4$, $SrF_2$, $NiBr_2$, $MnBr_2$, $VBr_3$, $TaBr_5$, $RuBr_3.XH_2O$, $RhBr_3$, $PdBr_2$, $HfBr_4$, $NbBr_5$, $FeBr_2$, $FeBr_3$, $TiBr_4$, $SrBr_2$, $NiI_2$, $MnI_2$, $RuI_3$, $RhI_3$, $PdI_2$ or $TiI_4$;

$(NH_4)_6H_2W_{12}O_{40}$ or $(NH_4)_6H_2Mo_{12}O_{40}$;

organometallic precursors such as metal carbonyl salts, for example, $Mo(CO)_6$, $W(CO)_6$, $Ni(CO)_4$, $Mn_2(CO)_{10}$, $Ru_3(CO)_{12}$, $Fe_3(CO)_{12}$ or $Fe(CO)_5$ and their alkyl and aryl derivatives;

acetates, for example, $Ni(ac)_2.4H_2O$, $Mn(ac)_2.4H_2O$, $Rh_2(ac)_4$, $Pd_3(ac)_6$, $Pd(ac)_2$, $Fe(ac)_2$, $Sr(ac)_2$, $Cu(ac)_2$, $Zn(ac)_2$, $Cd(ac)_2$ or $In(ac)_3$, where $ac=OOCCH_3$;

acetylacetonates, for example, $Ni(acac)_2$, $Mn(acac)_2$, $V(acac)_3$, $Ru(acac)_3$, $Rh(acac)_3$, $Pd(acac)_2$, $Hf(acac)_4$, $Fe(acac)_2$, $Fe(acac)_3$, $Sr(acac)_2$, $Sr(acac)_2.2H_2O$, $Cu(acac)_2$, $Ga(acac)_3$ or $In(acac)_3$, where $acac=CH_3C(O)CHC(O)CH_3$;

hexanoates, for example, $Mo[OOCH(C_2H_5)C_4H_9]_x$, $Ni[OOCCH(C_2H_5)C_4H_9]_2$, $Mn[OOCCH(C_2H_5)C_4H_9]_2$, $Nb[OOCCH(C_2H_5)C_4H_9]_4$, $Fe[OOCCH(C_2H_5)C_4H_9]_3$ or $Sr[OOCCH(C_2H_5)C_4H_9]_2$;

stearates, for example, $Ni(st)_2$, $Fe(st)_2$ or $Zn(st)_2$, where $st=O_2C_{18}H_{35}$;

amine precursors, for example, complexes of the form $[M(CO)_n(amine)_{6-n}]$ where M is a metal and $1 \leq n \leq 6$;

metal alkyl precursors, for example, $W(CH_3)_6$; or bis(ethylbenzene)molybdenum $[(C_2H_5)_yC_6H_{6-y}]_2Mo$ (y=1-4).

In one embodiment, the second precursor is a non-metal precursor. Non-limiting examples include a chalcogen precursor, such as, but not restricted to, an alcohol, an alkyl thiol or an alkyl selenol; a carboxylic acid; $H_2S$ or $H_2Se$; an organo-chalcogen compound, for example thiourea or selenourea; inorganic precursors, for example $Na_2S$, $Na_2Se$ or $Na_2Te$; phosphine chalcogenides, for example trioctylphosphine sulfide, trioctylphosphine selenide or trioctylphosphine telluride; octadecene sulfide, octadecene selenide or octadecene telluride; diphenyl dichalcogenides, for example diphenyl disulfide, diphenyl diselenide or diphenyl ditelluride; or elemental sulfur, selenium or tellurium. Particularly suitable chalcogen precursors include linear alkyl selenols and thiols such as octane thiol, octane selenol, dodecane thiol or dodecane selenol, or branched alkyl selenols and thiols such as tert-dibutyl selenol or tert-nonyl mercaptan, which may act as both a chalcogen source and capping agent. It has been found that the use of a slow-releasing chalcogen source provides controllable growth in such a synthesis method for 2D nanoparticles. In this context, a "slow-releasing chalcogen source" is defined as being a compound having a chalcogen-carbon bond that is broken when the compound acts as a chalcogen precursor in a nanoparticle synthesis reaction. In a further embodiment, the slow-releasing chalcogen source may initially decompose via the cleavage of a chalcogen-chalcogen bond, then in a subsequent step a carbon-chalcogen bond is broken when the compound acts as a chalcogen precursor in a nanoparticle synthesis reaction. Suitable slow-releasing chalcogen precursors include, but are not restricted to: compounds of the form R—S—R', wherein R is an alkyl or aryl group, X is a chalcogen and R' is H, alkyl, aryl or X—R" (wherein R" is alkyl or aryl). In a particular embodiment, the slow-releasing chalcogen source is a slow-releasing sulfur source such as 1-dodecanethiol (DDT).

Other suitable non-metal precursors include Group 15 precursors, such as, but not restricted to, $NR_3$, $PR_3$, $AsR_3$, $SbR_3$ (R=Me, Et, tBu, $^iBu$, $^iPr$, Ph, etc.); $NHR_2$, $PHR_2$, $AsHR_2$, $SbHR_2$ (R=Me, Et, Bu, Bu, Pr, Ph, etc.); $NH_2R$, $PH_2R$, $AsH_2R$, $SbH_2R_3$ (R=Me, Et, tBu, $^iBu$, $Pr^i$, Ph, etc.); $PH_3$, $AsH_3$; $M(NMe)_3$ where M=P, As, Sb; dimethyldrazine ($Me_2NNH_2$); ethylazide (Et-NNN); hydrazine ($H_2NNH_2$); $Me_3SiN_3$; tris(trimethylsilyl) phosphine; and tris(trimethylsilyl) arsine.

In one embodiment, a single-source precursor may act as both a metal and non-metal precursor. Suitable examples of single-source precursors include, but are not restricted to, alkyl dithiocarbamates; alkyl diselenocarbamates; complexes with thiuram, for example, $WS_3L_2$, $MoS_3L_2$ or $MoL_4$, where $L=E_2CNR_2$, E=S and/or Se, and R=methyl, ethyl, butyl and/or hexyl; $(NH_4)_2MoS_4$; $(NH_4)_2WS_4$; or Mo$(S^tBu)_4$.

The first and second precursors are combined, or the single-source precursor dissolved, in one or more solvents. The boiling point of the solvent(s) must be high enough to enable the solvent(s) to be heated to a sufficiently high temperature to effect the conversion of the first and second nanoparticle precursors, or the single-source precursor, to nanoparticles. In some embodiments, the one or more solvents may comprises a coordinating solvent. Examples of suitable coordinating solvents include, but are not restricted to: saturated alkyl amines such as, for example, $C_6$-$C_{50}$ alkyl amines; unsaturated fatty amines such as, for example, oleylamine; fatty acids such as, for example, myristic acid, palmitic acid, and oleic acid; phosphines such as, for example, trioctylphosphine (TOP); phosphine oxides such as, for example, trioctylphosphine oxide (TOPO); alcohols such as, for example hexadecanol, benzylalcohol, ethylene glycol, propylene glycol; and may include primary, secondary, tertiary and branched solvents. In some embodiments, the one or more solvents may comprises a non-coordinating solvent, such as, but not restricted to, a $C_{11}$-$C_{50}$ alkane. In some embodiments, the boiling point of the solvent is between 150° C. to 600° C., for example, 160° C. to 400° C., or more particularly 180° C. to 360° C. In one particular embodiment, the solvent is hexadecylamine. In another embodiment, the solvent is myristic acid. If a non-coordinating solvent is used, the reaction may proceed in the presence of a further coordinating agent to act as a ligand or capping agent. Capping agents are typically Lewis bases, for example phosphines, phosphine oxides, and/or amines, but other agents are available such as oleic acid or organic polymers, which form protective sheaths around the nanoparticles. Other suitable capping agents include alkyl thiols or selenols, include linear alkyl selenols and thiols such as octane thiol, octane selenol, dodecane thiol or dodecane selenol, or branched alkyl selenols and thiols such as tert-dibutyl selenol or tert-nonyl mercaptan, which may act as both a chalcogen source and capping agent. Further suitable ligands include bidentate ligands that may coordinate the surface of the nanoparticles with groups of different functionality, for example, $S^-$ and $O^-$ end groups.

In one embodiment, the solution is heated to a first temperature for a first time period. The first temperature may be in the range 50 to 550° C., for example 150 to 450° C., or more particularly 200 to 350° C. The first time period may be in the range 10 seconds to 5 hours, for example 2 minutes to 2 hours, or more particularly 5 minutes to 50 minutes. In a particular example, the solution is heated to a first temperature of approximately 260° C. for approximately 20 minutes.

In one embodiment, the solution is subsequently heated to a second temperature for a second time period, wherein the second temperature is higher than the first temperature. The second temperature may be in the range 80 to 600° C., for example 200 to 500° C., or more particularly 300 to 400° C. In a particular embodiment, the second temperature is the boiling point of the solution and the solution is heated to reflux. The second time period may be in the range 5 minutes to 1 week, for example 10 minutes to 1 day, or more particularly 20 minutes to 5 hours. In a particular example, the solution is heated to a second temperature of approximately 330° C. for approximately 20 minutes. Increasing the duration of the heating of the solution at the second temperature may increase the yield and/or alter the dimensions of the resulting 2D nanoparticles.

The 2D nanoparticles may be isolated from the reaction solution by any suitable technique. Examples include, but are not restricted to, centrifugation, filtration, dialysis, and column chromatography. Size-selective isolation procedures may be employed to extract 2D nanoparticles having similar dimensions and thus similar emissive properties.

Syntheses of nanoparticles in colloidal solutions are particularly favorable since they allow control over the shape, size and composition of the nanoparticles, and may offer scalability. Colloidal nanoparticles may also be surface-functionalized with ligands (capping agents), where the ligands may be chosen to impart solubility in a range of solvents. Ligands may also be used to control the shape of the resulting nanoparticles. The inherent ligands deposited on the nanoparticle surface during nanoparticle synthesis may be exchanged with alternative ligands to impart a particular function, such as improved solution processability in a particular solvent.

The choice of reagents and the reaction parameters, such as temperature(s) and time(s), may be adjusted to control both the lateral dimensions and the thickness of the 2D nanoparticles and thus their emissive properties, such as the wavelength (color) of light emitted.

The 2D nanoparticles produced by the methods described herein may be dissolved or dispersed in a suitable solvent to provide solution processability. Solution-processable 2D nanoparticles are particularly attractive for applications such as photoluminescent displays and lighting, electroluminescent displays and lighting, 2D heterostructure devices, catalysis (for example, the hydrogen evolution reaction, the oxygen evolution reaction, catalytic desulfurization, etc.), sensors, and biological imaging.

One particular exemplary embodiment of the invention is a simple method of producing 2D nanoparticles of $MoS_2$. First, a complex is formed comprising molybdenum and an amine. Molybdenum hexacarbonyl may be used as the molybdenum source. For a discussion of bonding in metal carbonyls see, e.g. C. Kraihanzel and F. Cotton, *Inorg. Chem.*, 1963, 2, 533 and R. Dennenberg and D. Darensbourg, *Inorg. Chem.*, 1972, 11, 72. Oleylamine may be used as the amine source not only because it is a liquid and provides ease of use but also because the double bond may provide some functional use by π-bonding to the metal center thereby aiding dissolution of the volatile $Mo(CO)_6$ that sublimes quite easily (see S. Ghosh, S. Khamarui, M. Saha and S. K. De, *RSC Adv.*, 2015, 5, 38971). The amine is preferably thoroughly degassed and then used to form a suspension of the pre-weighed molybdenum source and transferred back to the reaction flask. Because $Mo(CO)_6$ sublimes easily, it cannot be placed under vacuum and needs to be heated gently to ~150° C. in order to form the complex. The solution turns a greenish yellow then deep yellow/brown at 150° C. At this point, it may be heated rapidly to between about 250° C. and 300° C. DDT is then added rapidly and the solution left for a certain time.

In a further exemplary embodiment, a complex is formed comprising molybdenum and an amine. At 150° C., a sulfur source is added and the mixture is transferred to a syringe and rapidly injected into an additional quantity of the amine. The solution is heated to 260° C. for a first time period. The temperature is subsequently increased to reflux and held for a second time period.

Example 1: Preparation of $MoS_2$ Nanoparticles 0.132 g $Mo(CO)_6$ was added to a vial capped with a SUBA-SEAL® rubber septum [SIGMA-ALDRICH CO., LLC, 3050 Spruce Street, St. Louis Mo. 63103] in a glovebox.

In a round-bottom flask, 14 mL oleylamine were degassed for 2 hours at 100° C. and then cooled to room temperature.

10 mL of the degassed oleylamine was removed with a syringe and 2-3 mL injected into the vial containing $Mo(CO)_6$ and shaken well. Using a clean syringe/needle that was purged three times with nitrogen, the oleylamine/Mo$(CO)_6$ suspension was transferred back into the round-bottom flask.

A further 2-3 mL oleylamine were added to the vial containing the $Mo(CO)_6$. It was shaken well and the contents again transferred back to the round-bottom flask. This was repeated until all the oleylamine and $Mo(CO)_6$ were transferred to the round-bottom flask.

The reaction mixture was warmed gently to 150° C. and the flask shaken to dissolve any sublimed $Mo(CO)_6$.

The reaction mixture was then heated to 250° C.

0.25 mL DDT was injected rapidly.

The reaction was left for 30 minutes and a further 0.25 mL DDT was injected and again left for 30 minutes.

The reaction was then heated to 300° C. and 0.5 mL DDT was injected and left for 30 minutes.

The reaction mixture was cooled to room temperature.

To isolate the product, 20 mL acetone were added and the supernatant discarded.

20 mL toluene were then added followed by 60 mL acetone.

The mixture was centrifuged and the supernatant discarded.

10 mL hexane were then added followed by 20 mL acetone then 10 mL acetonitrile and centrifuged. The supernatant was discarded and the solid rinsed with acetone and finally dissolved in 5 mL of hexane. Brief sonication of the solid was needed to obtain full dissolution.

The solution was centrifuged and any remaining solids were discarded.

Example 2: Preparation of $MoS_2$ Nanoparticles

Synthesis was carried out under an inert $N_2$ environment.

0.132 g $Mo(CO)_6$ was added to a vial capped with a SUBA-SEAL® rubber septum in a glovebox.

14 g octadecane were degassed for 2 hours at 100° C. in a round-bottom flask, then cooled to room temperature.

2 g hexadecylamine and 2 g octadecane were degassed for 2 hours at 100° C. in a vial, then cooled to 40-50° C. and injected into the vial containing the $Mo(CO)_6$ and shaken well.

The reaction mixture was warmed gently to 150° C. and the vial shaken to dissolve any sublimed $Mo(CO)_6$, then cooled to room temperature to form a $Mo(CO)_6$-amine complex.

The round-bottom flask (containing 14 g octadecane) was then heated to 300° C.

The $Mo(CO)_6$-amine complex was warmed gently to ~40° C. until the solids melted, and 1.5 mL 1-dodecane thiol (DDT) were added. It was then immediately loaded into a syringe and rapidly injected into the round-bottom flask. The temperature was adjusted to ~260° C.

The reaction mixture was left for 8 minutes at 260° C.

To isolate the product, 40 mL propanol mixed with 10 mL acetonitrile were added, centrifuged at 4000 rpm for 5 minutes and the supernatant discarded.

Example 3: Preparation of $MoS_2$ Nanoparticles

In a 200-mL vial, hexadecylamine (10 g) and hexadecane (50 mL) were degassed under vacuum at 80° C. The hexadecylamine/hexadecane solution was added to $Mo(CO)_6$ (0.66 g) in a 250-mL round-bottom flask, and stirred at 120° C. to form a solution ("solution A").

In a 1-L round-bottom flask, hexadecane (50 mL) and hexadecylamine (5 g) were heated under vacuum at 80° C. for 1 hour. The solution was heated to 250° C., under $N_2$, to form a solution ("solution B"). At 250° C., 5-mL portions of solution A (maintained at 120° C.) were added to solution B every 5 minutes for 1 hour to form a solution ("solution C").

1-dodecanethiol (7.5 mL) was subsequently added slowly to solution C at 250° C., over 1 hour, using a syringe pump, before stirring for a further hour at 250° C. The solution was cooled to 60° C., then acetone (400 mL) was added, followed by centrifugation. The residual solids were dispersed in hexane (125 mL).

Example 4: Preparation of $MoS_2$ 2D Nanoparticles

In a nitrogen-filled glove box, $Mo(CO)_6$ (0.132 g) was added to a vial capped with a Suba-Seal® rubber septum.

Hexadecylamine (4 g) was degassed at 100° C. for 2 hours, in a vial, then cooled to 40-50° C. and injected into the vial containing the $Mo(CO)_6$, then shaken well.

The reaction mixture was warmed gently to 150° C. and the vial shaken to dissolve any sublimed $Mo(CO)_6$, forming an $Mo(CO)_{6-x}$—(amine)$_x$ complex (where $1 \leq x < 6$), and maintained just above the melting point of the solution. Separately, hexadecylamine (14 g) was degassed at 100° C. for 2 hours, in a round-bottom flask, then cooled to room temperature.

The round-bottom flask containing the hexadecylamine was heated to 300° C.

1-dodecanethiol (1.5 mL) was added to the $Mo(CO)_{6-x}$—(amine)$_x$ complex, then the mixture was immediately transferred to a syringe and rapidly injected into the round-bottom flask containing the hexadecylamine. The temperature was adjusted to ~260° C. and held for 40 minutes.

The temperature was then raised to reflux (330° C.) and held at that temperature for 20 minutes until a black precipitate formed.

The flask was cooled to 60° C. and toluene (30 mL) was added. The mixture was centrifuged at 7000 rpm for 5 minutes and the black material was separated and discarded. The supernatant was dried under vacuum, then acetonitrile (50 mL) was added, warmed, and the top clear layer was decanted and discarded to leave an oily layer. The process was repeated three times to remove excess hexadecylamine. The material was finally dissolved in propanol and filtered through a 0.2-μm PTFE filter.

The solution exhibited bright blue emission. The PL contour map (see FIG. 1) shows the emission wavelength (x-axis) plotted against excitation wavelength (y-axis) for the $MoS_2$ 2D nanoparticle solution. The material showed excitation wavelength-dependent emission, with the highest intensity emission centered around 430 nm when excited at around 370 nm.

Figure 2:
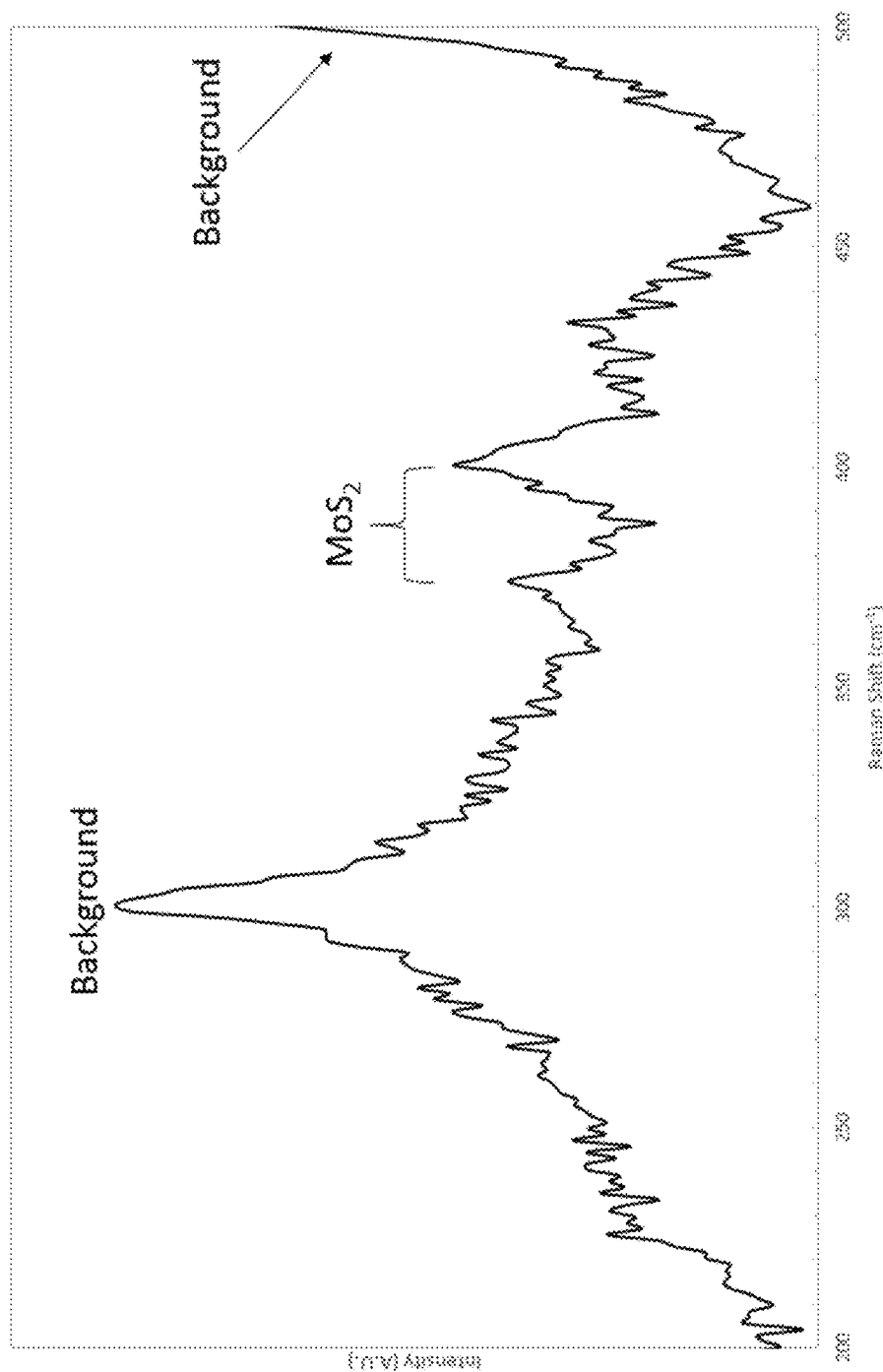
FIG. 2 is a Raman spectrum of $MoS_2$ 2D nanoparticles prepared according to Example 4.

The Raman spectrum (FIG. 2) shows peaks at 375 $cm^{-1}$ and 403 $cm^{-1}$, which are indicative of $MoS_2$. Note: the peaks at around 300 $cm^{-1}$ and 500 $cm^{-1}$ are from the background spectrum.

The foregoing presents particular embodiments of a system embodying the principles of the invention. Those skilled in the art will be able to devise alternatives and variations which, even if not explicitly disclosed herein, embody those principles and are thus within the scope of the invention. Although particular embodiments of the present invention have been shown and described, they are not intended to limit what this patent covers. One skilled in the art will understand that various changes and modifications may be made without departing from the scope of the present invention as literally and equivalently covered by the following claims.

What is claimed is:

1. A method of preparing $MoS_2$ nanoparticles comprising:
agitating a mixture of molybdenum hexacarbonyl (Mo(CO)$_6$) and degassed oleylamine in a sealed container to produce a suspension of oleylamine/$Mo(CO)_6$;
transferring the suspension of oleylamine/$Mo(CO)_6$ into a vessel containing degassed oleylamine to form a reaction mixture;
heating the reaction mixture to about 250° C.;
adding a first portion of 1-dodecane thiol (DDT) to the reaction mixture;
heating the reaction mixture at about 250° C. for about 30 minutes;
adding a second portion of 1-dodecane thiol (DDT) to the reaction mixture;
heating the reaction mixture at about 250° C. for about 30 minutes;
then heating the reaction mixture to about 300° C.;
then adding a third portion of 1-dodecane thiol (DDT) to the reaction mixture; and
heating the reaction mixture at about 300° C. for about 30 minutes.

2. The method recited in claim 1 further comprising:
isolating the nanoparticles; and
dissolving the isolated nanoparticles in a solvent.

3. A method of preparing $MoS_2$ nanoparticles comprising:
agitating a mixture of molybdenum hexacarbonyl (Mo(CO)$_6$), degassed octadecane, and degassed hexadecylamine in a sealed container to produce a first reaction mixture;
heating the reaction mixture to about 150° C. and then cooling the first reaction mixture to room temperature to form a $Mo(CO)_6$ amine complex;
heating a volume of degassed octadecane to about 300° C.;
warming the $Mo(CO)_6$ amine complex to about 40° C. to melt any solids;
adding 1-dodecane thiol (DDT) to the warmed $Mo(CO)_6$-amine complex to produce a second reaction mixture;
adding the second reaction mixture to the heated volume of degassed octadecane to form a third reaction mixture; and,
heating the third reaction mixture to about 260° C. for about 8 minutes.

4. A method of preparing $MoS_2$ nanoparticles comprising:
stirring a mixture of molybdenum hexacarbonyl (Mo(CO)$_6$), degassed hexadecane, and degassed hexadecylamine at about 120° C. to produce a first solution;
heating a mixture of hexadecane and hexadecylamine under vacuum at about 80° C. for about one hour and then heating the mixture of hexadecane and hexadecylamine to about 250° C. under $N_2$ to form a second solution;
adding portions of the first solution maintained at about 120° C. to the second solution about every 5 minutes for about 1 hour to form a third solution; and
adding 1-dodecane thiol (DDT) to the third solution at about 250° C. over a period of about 1 hour.

5. A method of preparing a luminescent composition of matter, the method comprising:
agitating a mixture of molybdenum hexacarbonyl (Mo(CO)$_6$) and degassed hexadecylamine at 40-50° C. in a sealed container to produce a first reaction mixture;
heating the first reaction mixture to about 150° C. to form a $Mo(CO)_6$-amine complex;
heating a volume of degassed hexadecylamine to 300° C.;
adding 1-dodecanethiol (DDT) to the first reaction mixture containing the $Mo(CO)_6$-amine complex to produce a second reaction mixture;
adding the second reaction mixture to the volume of degassed hexadecylamine heated to 300° C. to produce a third reaction mixture;
adjusting the temperature of the third reaction mixture to about 260° C.;
maintaining the temperature of the third reaction mixture at about 260° C. for about 40 minutes;
then increasing the temperature of the third reaction mixture sufficiently to reflux the hexadecylamine; and
refluxing the third reaction mixture for about 20 minutes to form a precipitate.

* * * * *